United States Patent [19]

Hummel

[11] Patent Number: 4,772,848
[45] Date of Patent: Sep. 20, 1988

[54] GAS MEASURING CHAMBER FOR PARAMAGNETIC MEASURING INSTRUMENTS

[75] Inventor: Heinz Hummel, Königstein-Johanniswald, Fed. Rep. of Germany

[73] Assignee: Leybold-Heraeus GmbH, Cologne, Fed. Rep. of Germany

[21] Appl. No.: 10,910

[22] Filed: Feb. 5, 1987

[30] Foreign Application Priority Data

Dec. 16, 1986 [DE] Fed. Rep. of Germany ....... 3642912

[51] Int. Cl.$^4$ .................... G01N 27/74; G01N 7/00; G01R 33/12
[52] U.S. Cl. ....................................... 324/204; 73/23; 73/27 A
[58] Field of Search .................. 324/204; 73/23, 27 A

[56] References Cited

U.S. PATENT DOCUMENTS

| | | | |
|---|---|---|---|
| 3,049,665 | 8/1962 | Hummel | 324/36 |
| 3,584,499 | 6/1971 | Hummel | 73/27 A X |
| 3,866,461 | 2/1975 | Machytka | 324/204 X |
| 4,683,426 | 7/1987 | Hummel | 324/204 |

FOREIGN PATENT DOCUMENTS

| | | |
|---|---|---|
| 177629 | 4/1986 | European Pat. Off. |
| 1079859 | 4/1960 | Fed. Rep. of Germany ..... 73/27 A |
| 1648924 | 1/1978 | Fed. Rep. of Germany . |
| 3400140 | 10/1984 | Fed. Rep. of Germany . |

OTHER PUBLICATIONS

"Ein neuer magnetischer Sauerstoff-Messer mit sehr Kurzer Einstellzeit und hoher Selektivität", Dr. Rer. Nat H. Hummel, Chemie-Ingenieur-Tecknik, 1968, vol. 19, pp. 947–951.

*Primary Examiner*—Gerard R. Strecker
*Attorney, Agent, or Firm*—Felfe & Lynch

[57] ABSTRACT

A paramagnetic measuring instrument comprises a magnetic circuit, formed from ferromagnetic material and having pole ends defining a discontinuity, and a gas measuring chamber disposed in the discontinuity between the pole ends. The measuring chamber includes a frame shaped outer part formed from nonmagnetic material and having a central opening extending between the pole ends; two ferromagnetic pole shoes each respectively disposed adjacent a separate one of the pole ends and extending into the opening of the outer part; two distribution channels disposed in the outer part on opposite sides of the measuring gap for supplying a measuring gas and a comparison gas, respectively, to the measuring gap; and inlet and outlet gas lines for supplying the measuring gas and the comparison gas, respectively, and removing the mixture formed from the measuring and comparison gases. According to the invention, the cross section of the opening of the outer part of the measuring chamber, as well as the pole faces, are rectangular. Furthermore, the distribution channels extend in straight lines, parallel to one another, at the two opposite shorter sides of the measuring gap. The distribution channels have a length corresponding to the length L of the shorter sides and have a height h and a depth t, respectively, which in each case is greater than the width W of the measuring gap.

4 Claims, 4 Drawing Sheets

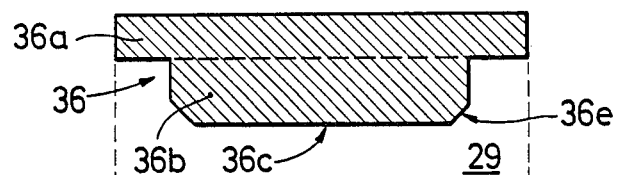
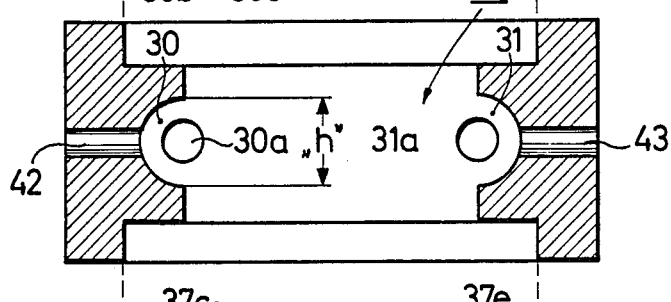
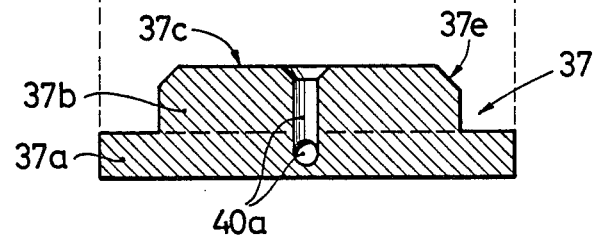
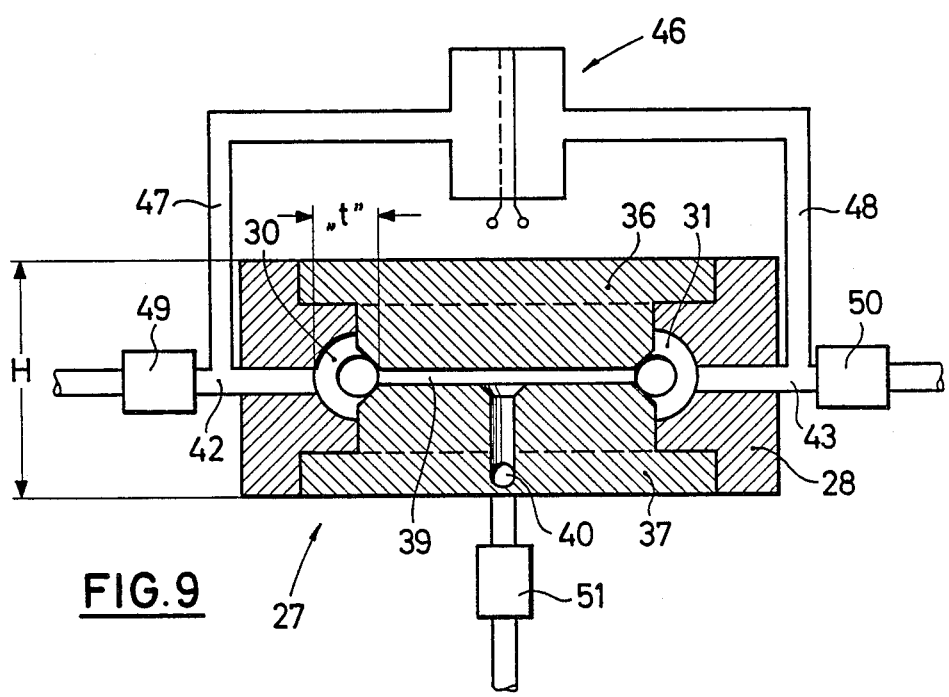

GAS MEASURING CHAMBER FOR PARAMAGNETIC MEASURING INSTRUMENTS

BACKGROUND OF THE INVENTION

The invention relates to a paramagnetic measuring instrument comprising a magnetic circuit, formed from ferromagnetic material and having pole ends defining a discontinuity, and a gas measuring chamber disposed in the discontinuity between the pole ends.

More particularly, the present invention relates to a gas measuring chamber for a paramagnetic measuring instrument which includes a frame shaped outer part formed from non-magnetic material and having a central opening extending between the pole ends of the magnetic circuit. Two ferromagnetic pole shoes, each respectively disposed adjacent a separate one of the pole ends and extending into the opening of the frame shaped outer part, have facing surfaces which form plane, parallel pole faces defining, between them, a "measuring gap". Two distribution channels are provided for supplying a measuring gas and a comparison gas, respectively, to the measuring gap. These channels are disposed in the frame shaped outer part on opposite sides of the measuring gap. Each distribution channel has an opening into the measuring gap. A first inlet gas line for supplying the measuring gas and a second inlet gas line for supplying the comparison gas are respectively connected to separate ones of the distribution channels. An outlet gas line is connected to the measuring gap for removing the mixture formed from the measuring and comparison gases.

The function of a paramagnetic measuring instrument of the type described above is based on the paramagnetic properties of certain gases, especially of oxygen. The fundamental principle, on which the measurement is based, as well as arrangements for its application are described in the paper "A New Magnetic Oxygen Meter with a Very Short Response Time and a High Selectivity" by Dr. Hummel in the journal "Chemie - Ingenieur - Technik", 1968, volume 19, pages 947 to 951. In principle, it is a question of alternately supplying the gas to be analyzed and a comparison gas of known composition to the gap of a magnetic circuit and of either determining the periodic changes in magnetic flux on the basis of a mechanically stimulated oscillation of the gases (alternating flow method) or of changing the magnetic flux periodically by electrical means and of measuring this effect on the pressure difference between the two sides of the measuring gap (alternating pressure method). The reference cited is concerned with the last-mentioned, alternating pressure method, whereas the alternating flow method is described in the German Pat. No. 1,079,859.

Methods and arrangements, tested for their practical value, are described in the cited German Pat. No. 1,079,859, as well as in the German Pat. No. 1,648,924. The two principles, on which the measurements are based, as well as a further, improved method of this type are also described in the European published patent application No. 0,177,629. The references cited also show the different possibilities of evaluating the test signals obtained electrically, namely the measurement of the change on the magnetic flux in the alternating flow method by a sensor coil in the magnetic circuit and the change in the pressure difference in the alternating pressure method by a pressure sensor, which is constructed, for example, as a capacitor microphone.

In all cases, there is considerable involvement of gas flows, in which gas oscillations, which are either the cause or the consequence of the effect measured depending on the principle employed for the measurement, are superimposed on the continuous gas flows (for the supply or exchange of gas). Moreover, a volume elements of the gaseous media may have very high flow velocities at least for short periods. As a rule, the measurement and comparison gases are supplied on opposite sides of the measuring gap and the gas mixture of measurement and comparison gases, which is unavoidably, obtained must be removed again continuously from the measuring system. The flow channels, required for this, are furthermore connected with both sides of a membrane or a piston, which either produces the alternating flow or measures the alternating pressure produced.

The measuring chamber of the paramagnetic measuring instrument, which is described generally above, must fulfill three essential requirements.

1. The use of the paramagnetic measurement principle must be possible, that is; there must be as narrow and as precise a measurement gap in the edge region as possible, with a strong field gradient.
2. With respect to the flow prerequisites, the measurement chamber must be so designed that it allows as rapid as possible a continuous gas replacement, as well as a pressure propagation.
3. It must be possible to produce the measuring chamber inexpensively and with great precision and high reproducibility.

The German Pat. No. 3,400,140 already describes an analyzer with a measuring chamber of the type described aboved, which largely fulfills the above requirements. This is made possible by a measuring gap in the form of an extremely flat, hollow cyinder which is surrounded on diametrically opposite sides by sickle-shaped bulges, which serve for supplying and distributing the measurement and comparison gases as well as for making the connection with the pressure measuring device (capacitor microphone). This shape is achieved owing to the fact that circular cylindrical pole shoes, which, between themselves, enclose the cylindrical measuring gap, are inserted from opposite sides into an oval recess in an external part of the measuring chamber. On the one hand, in this connection, it is desirable that the sickle-shaped bulges or distribution chambers be led as far as possible around the measuring gap in order to be able to have the gases flow through as large a portion of the inhomogeneous magnetic filed (field gradient) in the edge region of the measuring gap as possible. On the other hand, the mixing of the measurement and comparison gases in the ends of the sickle-shaped bulges, before they enter the measuring gap, must be prevented. In the sickle-shaped distribution chambers of the German Pat. No. 3,400,140, flow paths of greatly different lengths and different distances naturally arise between volume elements of measuring gas on the one hand and comparison gas on the other, lying opposite to one another in the direction of flow.

It is therefore an object of the invention to further improve the analyzer or measuring chamber of German Pat. No. 3,400,140 with regard to the flow relationships and the manufacturing possibilities.

SUMMARY OF THE INVENTION

For a paramagnetic measuring instrument having a measuring chamber of the type described at the beginning, this objective is accomplished, in accordance with the invention, by constructing the cross section of the opening of the outer part of the measuring chamber, extending parallel to the measuring gap, as well as the pole faces, in rectangular form, thereby having a pair of longer, and a pair of shorter parallel sides; by arranging the distribution channels to extend in a straight line, parallel to one another, at the two opposite shorter sides of the measuring gap; and by constructing the distribution channels to have a length corresponding to the length of the shorter sides and to have a height and a depth, respectively, which in each case is greater than the width of the measuring gap.

Due to the rectangular construction of the pole faces, the distances between edges of the measuring gap, lying opposite to one another in the direction of flow, are always of the same length, so tht flow short circuits are precluded. The rectangular construction of the pole faces has a further advantage in the formation of the magnetic circuit from thin transformer sheets, that, is, as a so-called "C-core". The pole shoes can therefore be inserted very accurately in the square or rectangular cross section of the magnetic circuit.

Due to the linear and parallel course of the distribution channels and in conjunction with the rectangular shape of the pole faces, the distribution channels can have the same cross section up to their ends, so that there is the least possible resistance to the flow or the exchange and oscillation of the gases. The two distribution channels thus form opposite storage spaces for the measuring gas, on the one hand, and the comparison gas, on the other. From these storage spaces, the individual gas flows can enter the measuring gap absolutely in parallel and with the same throughput per unit length of the edge of the measuring gap there.

The distributing channels may have a rectangular cross section. It is, however, particularly advantageous if the distribution channels are constructed as cylindrical boreholes, the axes of which lie in a plane of centers running between the pole faces. Such distribution channels can be produced in a particularly simple manner by a drilling process in the frame-shaped outer part of the measuring chamber, as will be understood from the following disclosure.

For further advantageous refinements and further objects of the invention, reference should now be made to the following detailed description of the preferred embodiments of the invention as illustrated in the accompanying drawings.

DESCRIPTION OF THE DRAWING

FIG. 6 shows a section through the object of FIG. 4 along the line VI—VI.

FIG. 7 shows one of the two pole shoes in an exploded representation relative to FIG. 6.

FIG. 8 shows the other of the two pole shoes in an exploded representation relative to FIG. 6.

FIG. 9 shows the assembly of the parts of FIGS. 6 to 8 conjunction with different gas lines for supplying measuring and comparison gases and carrying off the gas mixture formed therefrom.

DESCRIPTION OF THE PREFERRED EMBODIMENTS

Figure 1:
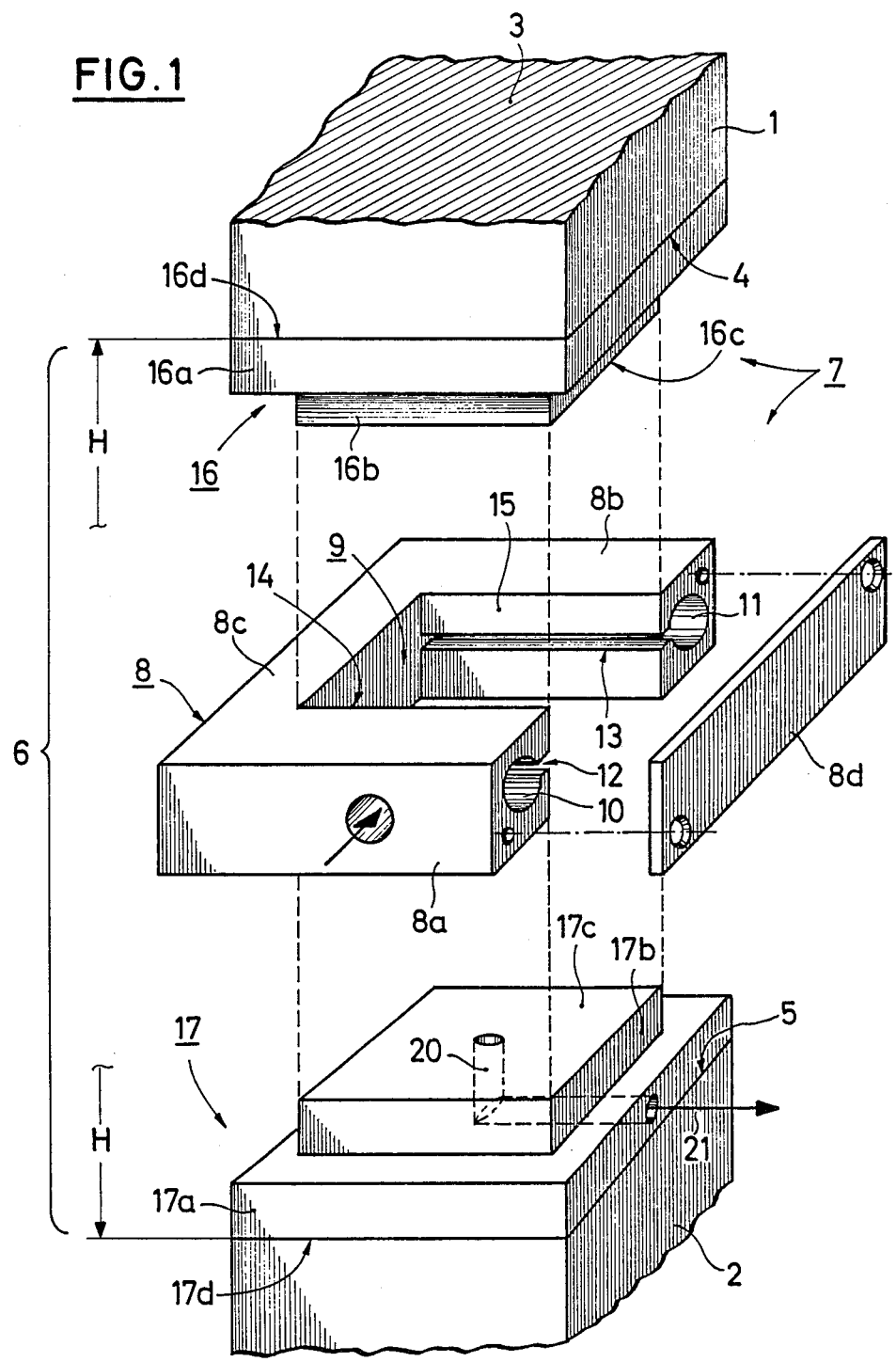
FIG. 1 shows a perspective exploded representation of all parts of the measuring chamber together with the ends of the magnetic circuit.

In FIG. 1, the two pole ends 1 and 2 of a magnetic circuit 3 are shown, which is constructed as a C-shaped magnet core, as shown in FIG. 7 of the initially cited paper in Chemie-Ingenieur-Technik on page 950. The pole ends 1 and 2 enclose or define a discontinuity, bounded by the plane-parallel pole faces 4 and 5, the distance between which is "H". Because the exploded mode of representation has been selected, the height "H" of course appears to be greater than it really is. In reality, the height dimension "H" corresponds to the height dimensions of the complete measuring chamber given in FIGS. 3 and 9. The magnetic circuit comprises a ferromagnetic material, preferably transformer sheets.

Figure 3:
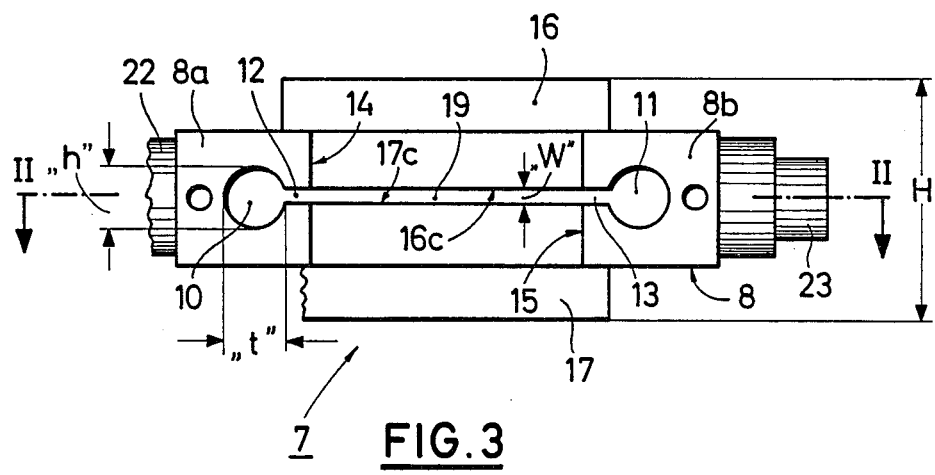
FIG. 3 shows a plan view of the upper part of FIG. 2 in the direction of the arrow III.
Figure 5:
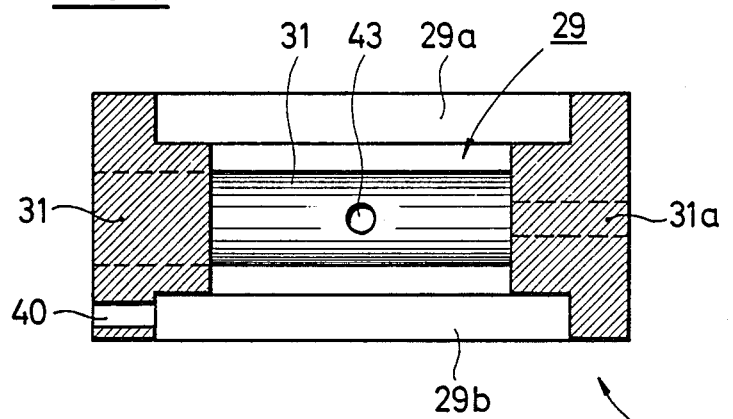
FIG. 5 shows a section along the line V—V of FIG. 4.

A measuring chamber 7, which is shown in the assembled state in FIG. 3, is disposed in the discontinuity 6. The measuring chamber 7 has a frame-shaped outer part 8 with a cuboid-shaped opening 9, which is surrounded by two cuboid-shaped legs 8a and 8b, a likewise cuboid-shaped yoke 8c and a plate-shaped end piece 8d. The enveloping surface of the whole outer part 8 of the measuring chamber once again is a cuboid, including also a cuboid with a square base surface.

In each of the two legs 8a and 8b, there is a cylindrical distribution channel 10 or 11, which passes through the whole length of each leg. The axes of the two distribution channels are parallel to one another and lie in a common plane, which in turn is parallel to the upper and lower bounding surfaces of the outer part 8 of the measuring chamber. On each side of this plane are the plane-parallel bounding surfaces of two gap openings 12 and 13, which lie in the mutually facing, parallel bounding surfaces 14 and 15 of the yokes 8a and 8b, which mark the limits of the opening 9. With this, the two distribution channels 10 and 11 open out over said gap openings 12 and 13 over the whole of the length of the legs 8a and 8b into the opening 9. The plane of centers through the two gap openings 12 and 13 then also defines the course of the measuring gap, which is described in greater detail below. The part of this plane of centers, bounded by the opening 9, can be regarded as the center of gravity of a surface. The normal to said plane, passing through this center of gravity of the surface, then also defines the axis of the opening 9, and this axis runs in the direction of the two ends 1 and 2 of the magnetic circuit 3.

The measuring chamber also includes two pole shoes 16 and 17, which are constructed and disposed in mirror symmetrical fashion. Each of these pole shoes has a flange 16a or 17a and an extension 16b or 17b, the rectangular surfaces facing one another forming the pole faces 16c and 17c. In the installed state, these pole faces mark the limits of a measuring gap 19, which will be dealt with in greater detail in connection with FIG. 3.

Figure 2:
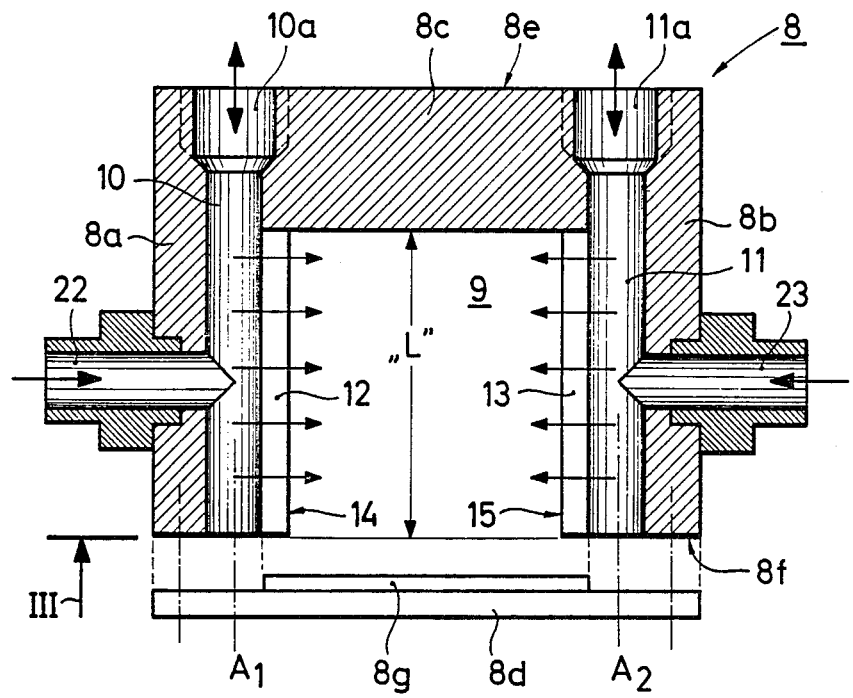
FIG. 2 shows a section along the line II—II of FIG. 3.

The pole shoes 16 and 17 consist of a ferromagnetic material. They may also be formed in one piece with the ends 1 and 2 of the magnetic circuit 3. In a multipart construction as shown in FIGS. 1 to 3, the outer surfaces 16d and 17d, facing away from the measuring gap 19, are inserted in the discontinuity 6 of the magnetic circuit, touching its plane-parallel wall surfaces 4 and 5. The surfaces 4 and 5 of the magnetic circuit 3 and the outer surfaces 16d and 17d of the pole shoes adjoining them are congruent. The dimensions of the pole faces 16c and 17c are such that the extensions 16b and 17b accurately fill up the opening over the whole of its extent. As soon as the flanges 16a and 17a are seated on outer part 8 of the measuring chamber, the accurately dimensionsed measuring gap 19 is formed between the pole faces 16c and 17c, as shown in FIG. 3.

It may furthermore be inferred from FIG. 1 that the lower pole shoe 17 has an angular borehole 20 with an opening in the pole face 17c. The function of this angular borehole is to carry away to the outside in the direction of arrow 21 the gas mixture formed in the center of the measuring gap from measuring and comparison gases, so that new measuring and comparison gases can be supplied to the measuring gap 19 through the distribution channels 10 and 11.

In addition, the following is evident from FIGS. 2 and 3. It can be seen from FIG. 2 that the two distribution channels 10 and 11 are drilled through the two legs 8a and 8b and through the rear bounding surface 8e of the yoke 8c. In the region of the yoke 8c, the distribution channels are expanded into tapped holes 10a and 11a, into which the gas lines can be inserted, which can be connected with an alternating pressure transducer or an alternating-pressure-responsive microphone, depending, reverence should now be made to the following detailed description of the preferred embodiments of the invention as illustrated in the accompanying drawings is used. In the event that such a connection is not required, it is possible to close off the tapped holes 10a and 11a by means of so-called dummy plugs. It may furthermore be inferred from FIG. 2 that the effective length of the distribution channels 10 and 11 is determined by the length "L", which in turn determines the length of the narrow sides of the measuring gap, which commences at the two gap openings 12 and 13. The gap openings 12 and 13 thus represent, in a manner of speaking, the narrow sides of the measuring gap, it being understood that the measuring gap may also have a square outline. The flow enters the measuring gap 19 alternately in essentially a laminar fashion in the direction of the parallel arrows.

Recess 9, the measuring gap 19 and the distribution channels 10 and 11 are closed off on the side opposite to the yoke 8c by the end piece 8d, which is screwed onto the front side 8f. A centering strip 8g protrudes slightly into the gap openings 12, 13 and into the measuring gap 19, in order to fix the spatial association.

The measuring gas on the one hand and the comparison gas on the other are supplied over two gas lines 22 and 23, of which only the connecting nipples are shown here. The gases are supplied approximately in the center of the length "L".

Further important dimensions of the arrangement are evident from FIG. 3, namely the height "h" and the depth "t" of the distribution channels, which are identical for cylindrical distribution channels (as in FIGS. 2 and 3) and correspond to the borehole diameter. Moreover, the dimension "W" of the gap width is given. It can be seen that the distribution channels have a continuous height "h" and depth "t", which individually are in each case greater than the gap width "W". With a conventional length of the measuring gap (indicated as "L"), these prescribed dimensions suffice to confer the function of storage spaces on the distribution channels 10 and 11, from which the flow enters the measuring gap 19 in parallel fashion in the direction of the arrows of FIG. 2.

In FIGS. 4 to 9, a measuring chamber 27 of a different construction is shown, the outer part 28 of which is constructed as a closed, rectangular (square) frame. The opening 29 also has a rectangular cross section here, but is offset step-fashion by the enlargements 29a and 29b. Before the opening 29 was made, some holes were drilled in the outer part of the measuring chamber. The outline of these holes is indicated by broken lines. These holes are the distribution channels 30 and 31, the gas offtake lines 42 and 42 for supplying measuring and comparison gases and the gas line 40 for discharging the gas mixture, formed from the measuring and comparison gases, away from the measuring gap. Connecting boreholes 30a and 31a lead from the inner ends of the distribution channels 30 and 31 to a pressure transducer or a pressure-responsive microphone, depending of which of the methods of measuring, initially described, is used. It is, however, also possible to close off the connecting boreholes 30a and 31a by dummy plugs. Such an alternate system is described in greater detail in connection with FIG. 9.

Figure 4:
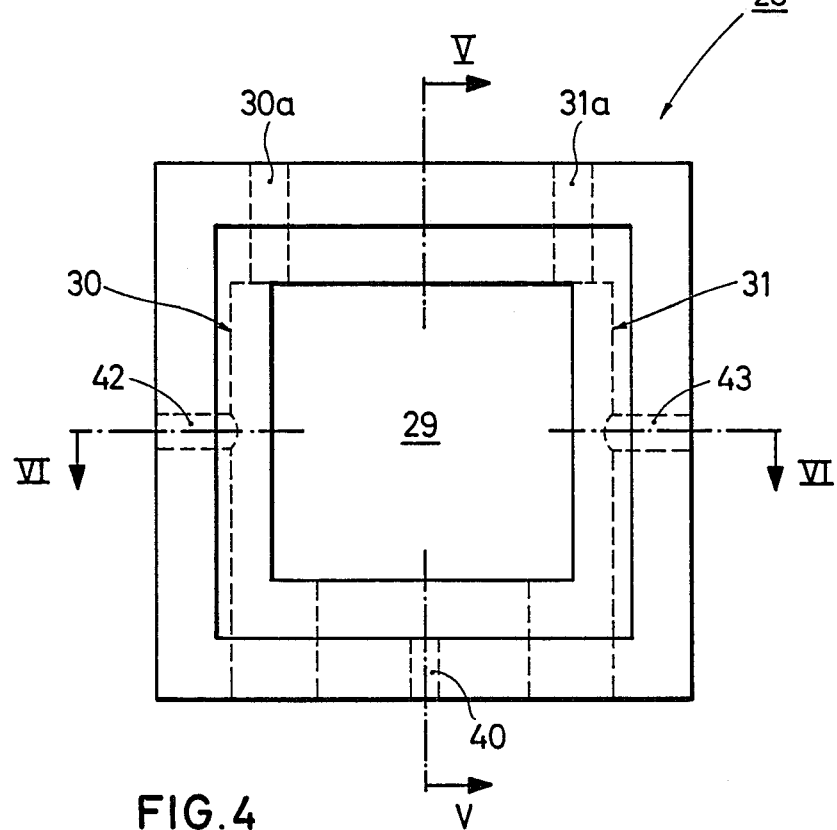
FIG. 4 shows a plan view of a different embodiment of the outer part of a measuring chamber.

As can be seen from FIG. 6, the two distribution channels 30 and 31 were intersected diametrically by the introduction of the opening 29 and thus form mutually facing semicylinders, into which the two gas lines 42 and 43 for the measuring and comparison gases open out. In the opening 29, which can be sized accurately, for example, with the help of a broaching tool, two pole shoes 36 and 37, which are constructed and disposed in mirror-image fashion, are now inserted. These pole shoes 36 and 37 are approximately complementary in shape to the opening 29, including its step-shaped enlargements 29a and 29b. As a result, these pole shoes each also have a flange 36a or 37a, an extension 36b or 37b and pole faces 36c and 37c. In the lower pole shoe 37, an anugular borehole is once again disposed which, when the pole shoe is installed as shown in FIG. 9, is flush with the gas takeoff line 40. The gas takeoff line 40 and the angular borehole 40a, moreover, have the same function as the angular borehole in FIG. 1. The pole shoes 36 and 37 are provided at two opposite narrow sides with bevels 36e and 37e, the purpose of which is evident from FIG. 9. By inserting the pole shoes 36 and 37 in the outer part 28 of the measuring chamber as shown in FIG. 4, a measuring gap 39 is formed between the pole faces 36c and 37c. The opposite, a narrow sides of the measuring gap 39 open out into the distribution channels 30 and 31, with which the pole shoes, owing to their bevels 36e and 37e, effect a gas distribution similar to that in the example of the operation shown in FIGS. 1 and 3. Here also, the outer part 28 of the measuring chamber and the pole shoes 36 and 37 are essentially bounded by rectangularly disposed edges and, more particularly, the pole faces 36c and 37c are also rectangular or square. The remaining dimension guidelines of the example of the operation shown in FIGS. 1 and 3 can also be employed to advantage with the example of the operation shown in FIGS. 5 to 9.

The measuring chamber 27 of FIG. 9, instead of the measuring chamber 7 of FIG. 3, is then pushed into the magnetic circuit 3. By means of FIG. 9, it is also shown how an alternating-pressure-responsive microphone 46, here a capacitor microphone, is connected to the distribution channels 30 and 31, if the taped holes 10a/11a (FIG. 2) or the connecting boreholes of FIG. 4 are not used for this purpose. In the case of FIG. 9, the alternating-pressure-responsive microphone 46 is connected over measuring lines 47 and 48 with the gas lines 42 and 43, and moreover within the flow restrictors 49 and 50, which mark the limits of the measuring system with respect to the outer flow channels. The gas takeoff line 40 is also equipped with such a flow restrictor 51.

The advantages of the two preferred embodiments of the invention can be summarized as follows.

1. There is laminar flow through the measuring cell with respect to the like flow of measuring and comparison gases, as well as with respect to the alternating flow, which is superimposed on the like flow for measurement purposes.
2. There is a minimum of attenuation on ducting the alternating pressure, which arises in the measuring gap, to the alternating-pressure-responsive microphone. There is also a similar advantage for the alternating flow method.
3. Turbulences and noise signals resulting therefrom are largely avoided due to the absence of sharp-edged transitions in the flow path.
4. The measuring effect is enhanced due to the utilization of the whole width of the measuring gap (the dimension"L") for the transfer of alternating pressure.
5. In comparison to circular measuring chambers, magnetic stray field losses are largely avoided.
6. Because of the use of rectangular pole shoes, the whole of their cross section can be utilized ideally.
7. In spite of the gas oscillation, a more distinct boundary layer can be maintained between the measuring and comparison gases.
8. Dead zones or unutilized zones as well as possible flow short circuits are largely avoided.

The gas mixture, formed from the measuring and comparison gases, need not be taken off over a central opening in the measuring gap, but may also be taken of in a side area of the measuring gap.

There has thus been shown and described a novel gas measuring chamber for a paramagnetic instrument which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention which is limited only by the claims which follow.

I claim:

1. In a paramagnetic measuring instrument comprising a magnetic circuit, formed from ferromagnetic material and having pole ends defining a discontinuity for accommodating a gas measuring chamber, and a gas measuring chamber disposed in the discontinuity between the pole ends, said measuring chamber including:
    a frame shaped outer part formed from nonmagnetic material and having a central opening extending between said pole ends;
    two ferrromagnetic pole shoes, each respectively disposed adjacent a separate one of said pole ends and extending into said opening of said outer part, the facing surfaces of said pole shoes forming plane, parallel pole faces which define a measuring gap between them;
    two distribution channels for supplying a measuring gas and a comparison gas, respectively, to said measuring gap, said channels being disposed in said outer part on opposite sides of said measuring gap, each distribution channel opening into said measuring gap;
    at least one first inlet gas line for supplying said measuring gas and at least one second inlet gas line for supplying said comparison gas, said first and second inlet gas lines being respectively connected to separate ones of said distribution channels; and
    at least one outlet gas line disposed in at least one of said pole shoes and opening into said measuring gap for removing the mixture formed from said measuring and comparison gases;
    the improvement wherein:
    (a) the cross section of said opening of said outer part of the measuring chamber extending parallel to said measuring gap, as well as said pole faces, is rectangular, thereby having a pair of longer and a pair of shorter parallel sides; and
    (b) said distribution channels extend in a straight line and are parallel to one another at the two opposite shorter sides of said measuring gap; said distribution channels have a length corresponding to the length of said shorter sides; and said distribution channels throughout have a height and a depth, respectively, which in each case is greater than the width of said measuring gap.

2. The gas measuring chamber as defined in claim 1, wherein the product of the height "h" and the depth "t" of each distribution channel is greater than 0.5 times the value of the product of the gap width "W" and the length "L" of the narrow side.

3. The gas measuring chamber as defined in claim 1, wherein the distribution channels are constructed as cylindrical boreholes, the axes of which run in the plane of centers between the pole faces.

4. The gas measuring chamber as defined in claim 1, wherein the outer part of the measuring chamber has a U-shaped main piece, in the two legs of which are disposed the distribution channels, which are connected over gap openings with the main opening, the side of said main piece opposite to the yoke being closed off by an end piece.

* * * * *